United States Patent
Dawkins et al.

(10) Patent No.: US 10,787,404 B2
(45) Date of Patent: Sep. 29, 2020

(54) METHODS FOR PRODUCING HALOGENATED PROPANES

(71) Applicant: OCCIDENTAL CHEMICAL CORPORATION, Dallas, TX (US)

(72) Inventors: John L Dawkins, Derby, KS (US); Darrell Hollis, Conway Springs, KS (US); Keith S. Kramer, Andover, KS (US); Brian Calderwood, Wichita, KS (US)

(73) Assignee: Occidental Chemical Corporation, Dallas, TX (US)

( * ) Notice: Subject to any disclaimer, the term of this patent is extended or adjusted under 35 U.S.C. 154(b) by 0 days.

(21) Appl. No.: 16/320,574

(22) PCT Filed: Jul. 24, 2017

(86) PCT No.: PCT/US2017/043469
§ 371 (c)(1),
(2) Date: Jan. 25, 2019

(87) PCT Pub. No.: WO2018/022488
PCT Pub. Date: Feb. 1, 2018

(65) Prior Publication Data
US 2019/0284118 A1    Sep. 19, 2019

Related U.S. Application Data

(60) Provisional application No. 62/366,674, filed on Jul. 26, 2016.

(51) Int. Cl.
*C07C 17/275* (2006.01)
*B01D 3/32* (2006.01)
(Continued)

(52) U.S. Cl.
CPC .......... *C07C 17/275* (2013.01); *B01D 3/322* (2013.01); *B01F 7/0025* (2013.01); *B01F 7/18* (2013.01);
(Continued)

(58) Field of Classification Search
CPC ....... C07C 17/10; C07C 17/25; C07C 17/275; C07C 17/38; C07C 17/04; C07C 19/01; C07C 21/04; C07C 17/383
See application file for complete search history.

(56) References Cited

U.S. PATENT DOCUMENTS 3,349,010 A * 10/1967 Plaster ................ B01D 3/4255
203/99
4,535,194 A    8/1985 Woodard
(Continued)

FOREIGN PATENT DOCUMENTS

EP    0 131 560 A1    1/1985

OTHER PUBLICATIONS

International Search Report and Written Opinion for corresponding PCT/US2017/043469 dated Sep. 20, 2017.

*Primary Examiner* — Jafar F Parsa
(74) *Attorney, Agent, or Firm* — Renner, Kenner; Arthur M. Reginelli

(57) ABSTRACT

A process of the type for producing chlorinated propanes by reacting carbon tetrachloride with ethylene within a tank reactor that includes a liquid reaction mixture and a headspace above the reaction mixture wherein ethylene gas diffuses from the liquid reaction mixture into the headspace while agitating the reaction mixture, the improvement comprising transferring ethylene within the headspace back into the reaction mixture through a conduit within the mixing device that agitates the reaction mixture.

19 Claims, 4 Drawing Sheets

(51) Int. Cl.
  *B01F 7/00* (2006.01)
  *B01F 7/18* (2006.01)
  *B01F 15/00* (2006.01)
  *B01J 23/745* (2006.01)
  *B01J 35/02* (2006.01)
  *C07C 17/383* (2006.01)
  *C07C 17/361* (2006.01)
  *B01J 19/18* (2006.01)
  *B01J 19/00* (2006.01)

(52) U.S. Cl.
  CPC ....... *B01F 15/00915* (2013.01); *B01J 19/006* (2013.01); *B01J 19/18* (2013.01); *B01J 23/745* (2013.01); *B01J 35/026* (2013.01); *C07C 17/361* (2013.01); *C07C 17/383* (2013.01); *B01F 2215/0036* (2013.01); *B01J 2219/00182* (2013.01); *B01J 2219/00768* (2013.01)

(56) References Cited

U.S. PATENT DOCUMENTS

| | | | |
|---|---|---|---|
| 4,605,802 A | 8/1986 | Astrologes | |
| 6,313,360 B1 * | 11/2001 | Wilson | C07C 17/278 570/257 |
| 8,912,372 B2 * | 12/2014 | Wilson | C07C 17/10 570/227 |
| 2004/0225166 A1 | 11/2004 | Wilson et al. | |
| 2014/0081056 A1 | 3/2014 | Wilson et al. | |

* cited by examiner

METHODS FOR PRODUCING HALOGENATED PROPANES

This application is a National-Stage application of PCT/US2017/043469 filed on Jul. 24, 2017, which claims the benefit of U.S. Provisional Application Ser. No. 62/366,674 filed on Jul. 26, 2016, which are incorporated herein by reference.

FIELD OF THE INVENTION

Embodiments of the present invention are directed toward methods for the production of halogenated propanes prepared by reacting carbon tetrachloride with an olefin.

BACKGROUND OF THE INVENTION

Industrially important hydrofluorocarbons, such as those used as refrigerants and blowing agents, are prepared from hydrochlorocarbon feedstocks. For example, 1,1,1,3,3-pentafluoropropane (HFC-245fa) is a widely employed hydrofluorocarbon that, according to U.S. Pat. No. 6,313,360, can be prepared from a 1,1,1,3,3-pentachloropropane (HCC-240fa) feedstock.

According to U.S. Pat. No. 6,313,360, the 1,1,1,3,3-pentachloropropane can be synthesized by reacting carbon tetrachloride with vinyl chloride in the presence of an iron catalyst and tributylphosphate. Vinyl chloride is fed to the reactor as a liquid or vapor, and metallic iron, preferably in the form of a slurry within carbon tetrachloride, is added to the reactor. The reactor contents are continually drawn from the reactor, preferably through a sedimentation tube, in order to maintain the unconverted metallic iron within the reactor. This process is enhanced by drawing the reactor effluent from a still zone created within the reactor. The reactor effluent is distilled to recover catalyst and ultimately isolate the desired 1,1,1,3,3-pentachloropropane product. U.S. Publ. No. 2012/0310020 suggests that the formation of polyvinyl chloride within the reactor can be reduced by feeding the vinyl chloride as a vapor through a dip tube or sponge-type gas diffuser into a reactor precharged with carbon tetrachloride, tributylphosphate, and iron powder.

Hydrofluoroolefins have been targeted as replacements for hydrofluorocarbons. For example, 2,3,3,3-tetrafluoropropene (HFO-1234yf) has been proposed as a replacement for 1,1,1,2-tetrafluoroethane (R-134a) as a refrigerant in automobile air conditioners. As with the hydrofluorocarbons, chlorinated organics play an important role in the synthesis of hydrofluoroolefins. For example, U.S. Publ. Nos. 2009/0030247 and 2014/0256995 teach that 1,1,2,3-tetrachloropropene (HCC-1230xa) is an advantageous starting molecule for the production of 2,3,3,3-tetrafluoropropane (HFO-1234yf).

U.S. Publ. No. 2009/0216055 teaches that 1,1,2,3-tetrachloropropene (HCC-1230xa) can be prepared by dehydrochlorinating 1,1,1,2,3-pentachloropropane, and that the 1,1,1,2,3-pentachloropropane can be prepared within a single reactor by reacting 1,1,1,3-tetrachloropropane (HCC-250fb) with chlorine in the presence of a Lewis acid. According to U.S. Publ. No. 2004/0225166, 1,1,1,3-tetrachloropropane can be synthesized by reacting carbon tetrachloride with ethylene in the presence of metallic iron, dissolved iron (II), iron (III) compounds, and an organophosphate cocatalyst. U.S. Publ. No. 2004/0225166 teaches that the reactor in which the carbon tetrachloride and ethylene are reacted is agitated to provide adequate contact of the liquid reactants with the surface of the metallic iron, to provide adequate contact of the liquid reactants with the vapor in the reactor headspace so that ethylene is readily dissolved in the liquid, and to provide adequate contact of the reaction mixture with heat-transfer surfaces to thereby enable adequate temperature control.

Because 1,1,1,3-tetrachloropropane is an important halogenated propane, there remains a desire to improve synthetic techniques employed in its preparation.

SUMMARY OF THE INVENTION

One or more embodiments of the present invention provide a process of the type for producing chlorinated propanes by reacting carbon tetrachloride with ethylene within a tank reactor that includes a liquid reaction mixture and a headspace above the reaction mixture wherein ethylene gas diffuses from the liquid reaction mixture into the headspace while agitating the reaction mixture, the improvement comprising transferring ethylene within the headspace back into the reaction mixture through a conduit within the mixing device that agitates the reaction mixture.

Other embodiments of the present invention provide a process of the type for producing chlorinated propanes by reacting carbon tetrachloride with an olefin in the presence of an insoluble or partially soluble catalyst or catalyst precursor within a liquid reaction mixture, the improvement comprising charging the catalyst or catalyst precursor to the reaction mixture within a slurry that is continuously agitated.

Yet other embodiments of the present invention provide a process of the type for preparing chlorinated propanes by reacting carbon tetrachloride with an olefin in the presence of an insoluble or partially soluble catalyst or catalyst precursor within a liquid reaction mixture being continuously stirred within a tank reactor, the improvement comprising removing the chlorinated propane product from the tank reactor from a still zone within said reactor.

Still other embodiments of the present invention provide a process of the type for purifying a crude chlorinated propane stream including iron and optionally iron compounds by distillation techniques, the improvement comprising heating the crude product stream within a reboiler operating at conditions that inhibit the reaction or formation of deposits within the distillation column and the reboiler.

DETAILED DESCRIPTION OF ILLUSTRATIVE EMBODIMENTS

Figure 1:
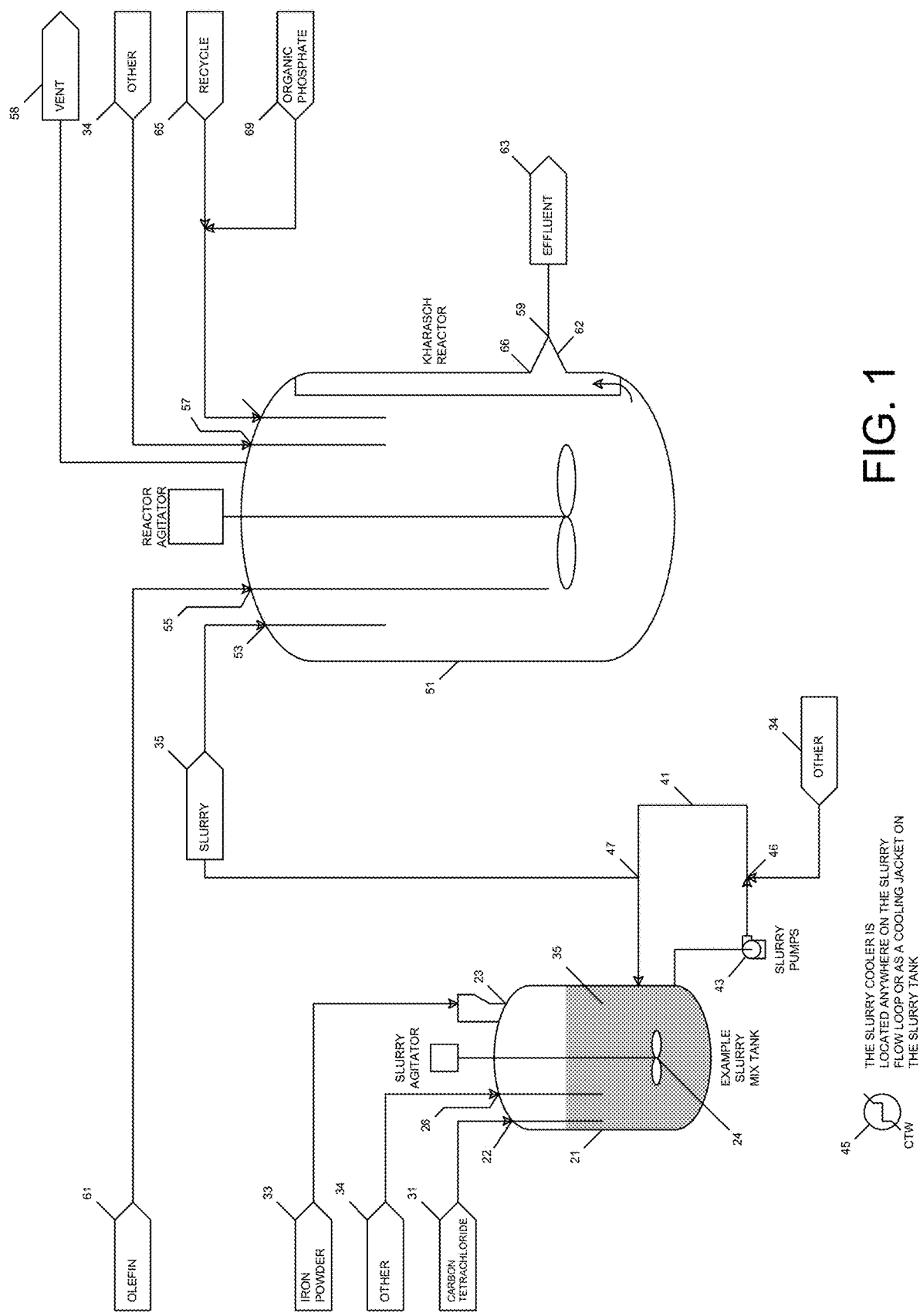
FIG. 1 is a schematic view of a system for the preparation of chlorinated propanes according to embodiments of the invention including a slurry loop.

Embodiments of the invention are based, at least in part, on the discovery of a method for producing chlorinated propanes. According to one or more embodiments, carbon tetrachloride is reacted with ethylene within a reactor that is mixed with an aspirating agitator. Thus, while the prior art suggests the need to mix the liquid contents (i.e., carbon tetrachloride) for the purpose of providing adequate contact between the carbon tetrachloride and ethylene, which is in the vapor phase, it is now contemplated that reaction efficiencies can be realized by transferring ethylene located within the headspace of the reactor to a reaction zone (i.e. into the liquid phase) through the use of an aspirating agitator.

According to other embodiments, chlorinated propanes are prepared by reacting carbon tetrachloride with an olefin (e.g. ethylene) in the presence of an iron-based catalyst. Iron is charged to the reactor from a continuously stirred slurry tank operating within a circulation loop. Thus, while the prior art suggests the desire to deliver iron metal within a slurry with carbon tetrachloride, it is now contemplated that production efficiencies can be realized by improving the delivery of the iron metal within the slurry. Additionally, this dynamic circulation loop offers the ability to deliver other materials, such as other catalytic materials or ligands, to the reactor.

According to yet other embodiments, chlorinated propanes are prepared by reacting carbon tetrachloride with an olefin (e.g. ethylene) in the presence of an iron-based catalyst, and the chlorinated propanes are removed from the reaction zone through a conically-shaped effluent nozzle drawing from a still zone created within the reactor. In one or more embodiments, the still zone is configured to minimize liquid flow velocity and thereby maximize iron sedimentation while allowing gaseous reactants to rise to the reactor headspace. Thus, while the prior art suggests advantages associated with withdrawing reactor fluid from a still zone, it is now contemplated that specific reactor designs can give rise to process efficiencies.

Still further, embodiments of the invention are directed toward purification techniques wherein chlorinated propanes (e.g. 1,1,1,3-tetrachloropropane) are separated from heavier compounds, including catalytic materials (e.g. iron species), by using a distillation technique that heats the liquid mixture within a forced circulation reboiler. The flow velocity and heat flux are maintained to prevent fouling within the distillation system. Indeed, it has been discovered that localized hot spots within the distillation system cause catalyst residues to bake onto the surfaces of the system. Thus, while the prior art proposes distillation techniques to purify chlorinated propanes, it is now contemplated that specific distillation systems can give rise to process efficiencies.

Process Overview

As suggested above, the processes of the invention generally relate to the preparation of chlorinated hydrocarbons by reacting carbon tetrachloride with an olefin. These reactions are generally known in the art, and therefore U.S. Pat. No. 6,313,360 and U.S. Publ. Nos. 2004/0225166 and 2009/0216055 are incorporated herein by reference. Practice of embodiments of the invention are not necessarily limited by the olefin employed as a reactant, although common olefins for use in these reactions include ethylene and vinyl chloride. As the skilled person appreciates, ethylene is a gaseous olefin, and therefore embodiments of the invention may provide distinct advantages where ethylene is employed as a reactant. Other embodiments may be particularly beneficial where vinyl chloride is employed as a reactant. In any event, the following embodiments may be described with reference to a particular olefin (e.g. ethylene), although the skilled person will appreciate that other olefins can likewise be used. Also, the reaction between carbon tetrachloride and an olefin can be catalyzed by using a variety of catalytic species, many of which are or derive from species that are insoluble or only partially soluble in the reaction medium. A common catalyst or catalyst precursor is iron, and therefore embodiments of the invention may be described with reference to iron, but the skilled person will appreciate that embodiments of the invention can likewise be extended to other insoluble or partially soluble catalysts or catalyst precursors. Additionally, the skilled person appreciates that these insoluble or partially soluble catalysts may be used in conjunction with cocatalysts or ligands, which are believed to complement the catalyst; for example, tributylphosphate has been used in conjunction with an iron catalyst. Thus, while embodiments of the invention may be described with reference to tributylphosphate as a cocatalyst or ligand used in conjunction with iron, the skilled person will appreciate that the invention can be extended to the use of other cocatalysts or ligands.

One or more processes of the present invention can be described with reference to FIG. 1. As shown, system 11 includes iron slurry mix tank 21, which is in fluid communication with reactor 51 (which may be referred to as addition reactor 51) through a conduit loop 41. Slurry tank 21 receives carbon tetrachloride 31 through inlet 22 and iron powder 33 through inlet 23. Slurry tank 21 may also optionally receive other materials 34, such as additional solvents, catalysts, catalyst ligands, or recycle streams captured downstream in the process, through inlet 26. In one or more embodiments, carbon tetrachloride 31 may be fed continuously, or in other embodiments it may be periodically injected, into slurry tank 21 through inlet 22. Likewise, iron powder 33 may be periodically added to slurry tank 21, or in other embodiments, iron powder 33 may be continuously charged to slurry tank 21 by employing continuous feeding apparatus. For example, iron powder 33 can be charged to slurry tank 21 by employing a dustless bucket tipper.

A slurry 35 of carbon tetrachloride 31 and iron powder 33 is formed by agitating the mixture within slurry tank 21 via one or more mixing elements 24, which may include agitation devices or baffles. Mixing elements 24 may be operated in a manner to substantially disperse the catalyst (e.g. iron) within the chlorinated hydrocarbon liquid (e.g. carbon tetrachloride); in particular embodiments, agitation is sufficient to achieve a substantially homogenous concentration of the catalyst within the carbon tetrachloride.

Slurry 35 is continuously circulated through a conduit loop 41 via one or more pumps 43 that are upstream of reactor 51, which pumps may also advantageously maintain pressure within loop 41. Adequate pressure may also be maintained within loop 41 through the assistance of a back-pressure valve 46, which is downstream of where loop 41 delivers slurry 35 to reactor 51 (i.e. downstream of valve 47 within loop 41). Slurry 35 moving through loop 41 may be heated or cooled by heating or cooling elements 45. Other materials 34, such as those described above, may also optionally be injected into loop 41. In one or more embodiments, mixing of the various constituents within slurry 35 can be enhanced by one or more in-line mixers, which are not shown. Circulation loop 41 also includes valve 47 that, when in the open position, allows slurry 35 to feed reactor 51. When valve 47 is in its closed position, slurry 35 circulates through loop 41 back to mix tank 21. Valve 47 may include a control valve or solenoid valve that can be controlled by a signal flow sensor or similar device.

Reactor 51 receives slurry 35 from loop 41 via inlet 53. Reactor 51 also receives olefin 61, such as ethylene, via inlet 55. Additionally, and as will be explained in greater detail below, reactor 51 may also optionally receive other material inputs 34, such as those described above, via additional inlet 57. Reactor effluent 63 exits reactor 51 at outlet 59. Volatiles can be vented through outlet 58.

In one or more embodiments, the flow of slurry 35 into reactor 51, which flow is at least partially regulated by valve 47, can be proportional to the olefin 61 feed rate into reactor 51.

In one or more embodiments, loop 41 is maintained at a pressure that is greater than the pressure within reactor 51; in particular embodiments, the pressure within loop 41 is sufficient to create flow into reactor 51 (when valve 47 is open) while taking into account potential gravitational assistance. As the skilled person will appreciate, sufficient pressure can be maintained within loop 41 while valve 47 provides flow into reactor 51 by back-pressure valve 46. Valve 46 may include a control valve or solenoid valve that can be controlled by a signal flow sensor or similar device. In one or more embodiments, temperature controls (e.g. element 45) provides cooling to maintain the temperature of slurry 35 below the boiling point of the chlorinated hydrocarbon (e.g. below 77° C. for carbon tetrachloride). In particular embodiments, the loop temperature is maintained at from about 0 to about 80° C., in other embodiments from about 5 to about 60° C., and in other embodiments from about 10 to about 40° C.

In one or more embodiments, the concentration of iron powder 33 within slurry 35 may be represented as a percent solids within the weight of liquid. In one or more embodiments, the percent solids iron powder within slurry 35 may be from about 0.02 to about 5.0 wt %, in other embodiments from about 0.03 to about 1.0 wt %, and in other embodiments from about 0.05 to about 0.2 wt %.

Addition Reactor

As indicated above, carbon tetrachloride reacts with olefin, such as ethylene, in the presence of a catalytic species, such as iron powder or derivatives thereof, to produce a chlorinated propane within reactor 51. In particular, carbon tetrachloride reacts with ethylene to produce 1,1,1,3-tetrachloropropane. In this regard, U.S. Publ. No. 2004/0225166 and 2009/0216055 are incorporated herein by reference.

Reactor 51 can be further described with reference to FIG. 2, which shows slurry 35 entering reactor 51 at inlet 53, as well as olefin 61 (e.g. ethylene) entering at inlet 55, and other optional materials, such as tributylphosphate ligand 69 and catalyst recycle stream 65, entering via inlet 57. The contents of the reactor form a liquid level 67, which is the liquid level upon aeration, and the skilled person will appreciate that the liquid level will be lower when still (i.e. not aerated). Reactor 51 may generally include a tank reactor of the type known in the art (e.g. a CSTR).

In one or more embodiments, the charging of slurry 35, olefin 61, and other materials 69, 65, takes place by injecting the materials below the liquid level 67 within reactor 51. As the skilled person will appreciate, this may take place by the use of dip tubes, as well as various nozzles or diffusion devices. In particular embodiments, olefin 61 is injected at a location proximate to the bottom end 71 of reactor 51. In still more particular embodiments, olefin 61 is injected at or near mixing elements 73 of mixing device 75. In one or more embodiments, one or more of the reactants or catalysts may be injected above liquid level 67 (i.e. within the reactor head space); advantageously, the use of an aspirating agitator allows for the introduction of gaseous materials into the head space since the agitator will ultimately deliver the gaseous materials to the reaction zone. As indicated above, reactor effluent 63 exits reactor 51 via outlet 59.

In one or more embodiments, agitation device 75 includes a conduit that provides gaseous communication between headspace 68 and liquid mixture (i.e. slurry 35) below the liquid level 67. As a result, volatile compounds, especially ethylene, within the headspace can be returned to liquid mixture 64 to facilitate the desired reaction. In one or more embodiments, agitation device 75 is an aspirating agitator. As the skilled person appreciates, these agitators draw gaseous materials (e.g. ethylene) from the head space and reintroduce the gaseous materials into the reaction zone (i.e. into liquid mixture 64). In one or more embodiments, agitation device 75 is operated at a power to volume ratio of at least 10 kilowatts per cubic meter ($kW/m^3$), in other embodiments, at least 30 $kW/m^3$, and in other embodiments at least 50 $kW/m^3$, and in other embodiments from about 10 to about 100 $kW/m^3$.

Figure 2:
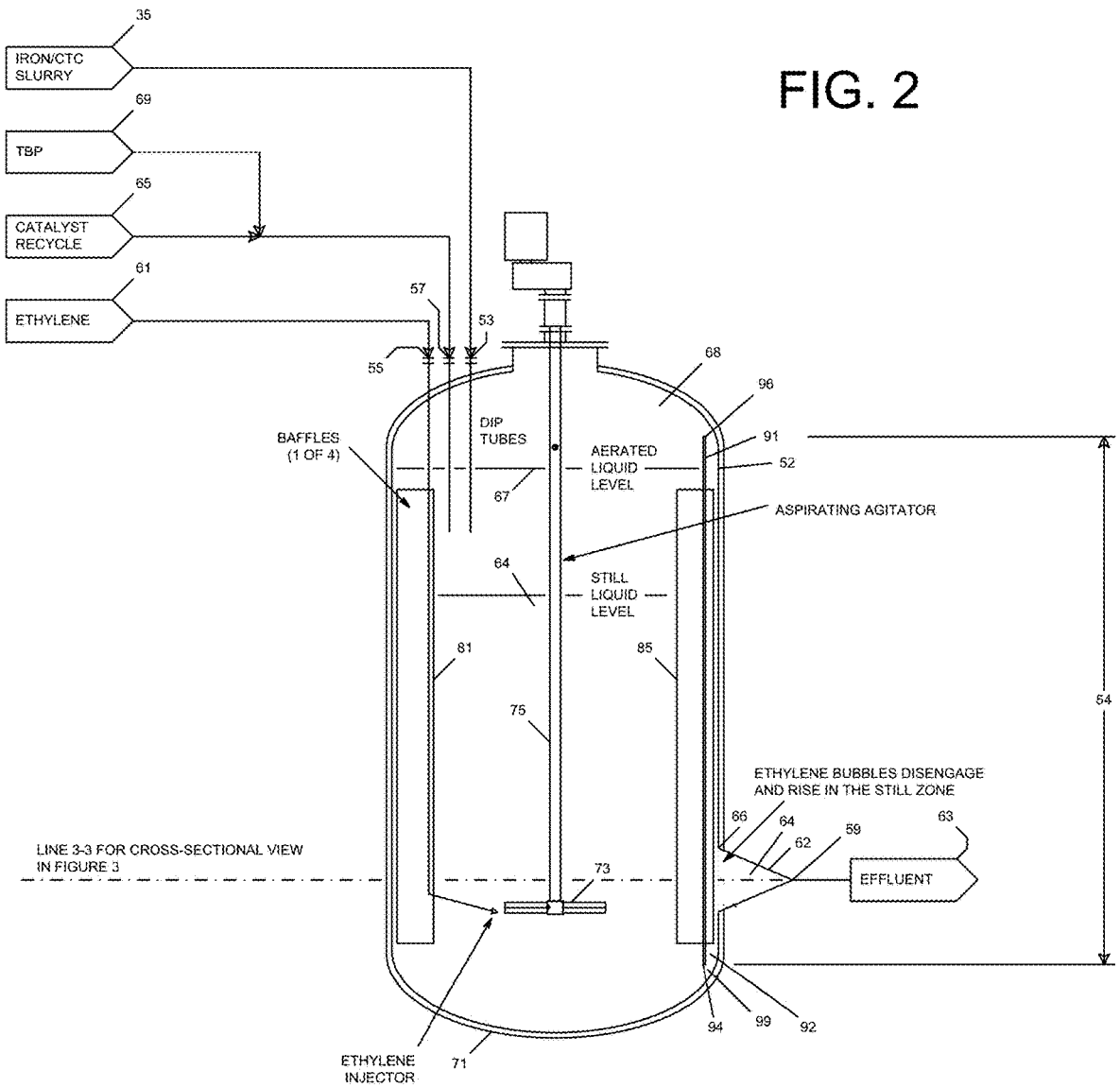
FIG. 2 is a sectional view of an addition reactor employed in the practice of one or more embodiments of the invention.
Figure 3:
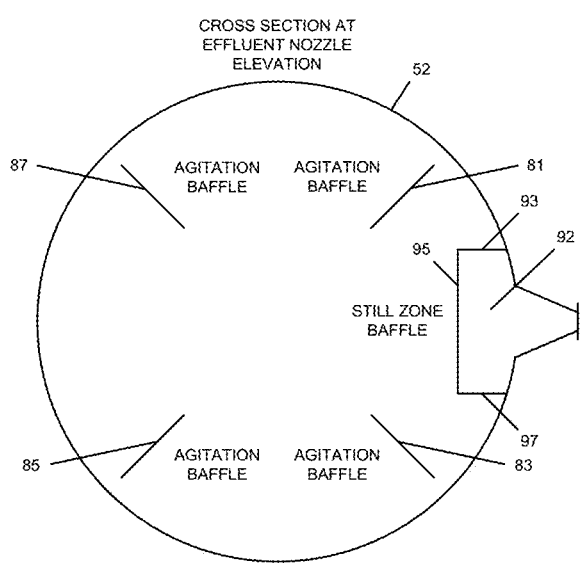
FIG. 3 is a sectional view taken substantially along line 3-3 of FIG. 2.

As also shown in FIG. 2, as well as FIG. 3, reactor 51 includes one or more agitation baffles 81, 83, 85, and 87. Each of these respective agitation baffles (81, 83, 85, 87) are attached to the wall of the reactor (or to the top or bottom of the reactor). The dimensions and geometry of agitation baffles are known in the art. As best shown in FIG. 2, reactor 51 is equipped with a still-zone baffle 91. Still-zone baffle 91 includes opposed walls 93, 97, which are each respectively attached to circumferential wall 52 of reactor 51. Still-zone baffle 91 also includes interconnecting wall 95 connecting opposed walls 93, 97 to thereby form still zone 92. Still zone baffle 91 partially extends across the height 54 of wall 52 in order to provide a baffle gap 99 (best shown in FIG. 2) proximate to bottom 71 of reactor 51. Stated another way, still-zone baffle 91 has a height that extends above liquid level line 67 at its upper end 96, and at its lower end 94 does not contact bottom 71 of reactor 51 so as to provide a gap 99 through which liquid can flow. Still-zone baffle 91 is positioned within reactor 51 to surround outlet 59. As a result, reactor effluent 63 must enter still zone 92 formed by still-zone baffle 91 via baffle gap 99 in order to exit outlet 59.

As a result of this configuration, still-zone baffle 91 shields outlet 59 from direct agitation caused by agitation device 75. Gaseous bubbles, such as ethylene within liquid medium 64, therefore have an unrestricted path to rise out of still-zone 92 into the reactor headspace 68. Likewise, the configuration of still-zone baffle 91, which impacts still-zone 92, provides for a low liquid flow velocity as the reactor contents enter baffle gap 99 and exit outlet 59. This low velocity promotes iron powder sedimentation. As the skilled person will appreciate, by inhibiting iron powder from exiting reactor 51, the iron powder can be recirculated within the reactor so that it can be converted to soluble species by reaction or interaction with one or more constituents within the reactor. Thus, with the unrestricted path for gaseous materials to leave still-zone 92 and with the decreased flow velocity promoting iron powder sedimentation, the amount of gaseous reactants (e.g. ethylene) and iron powder exiting reactor 51 through outlet 59 is minimized. In these or other embodiments, outlet 59 is equipped with a conically shaped effluent nozzle 62, wherein wide end 66 is attached to reactor wall 52. This configuration further inhibits gas entrainment within effluent 63. Also, the height of outlet 59, relative to the height of the reactor, is designed to avoid substantial or appreciable turbulence that is present at the bottom of the reactor. The skilled person will appreciate that outlet 59 is nonetheless positioned relatively low within the reactor to provide for the ability to empty the contents of the reactor when desired.

In one or more embodiments, the velocity of liquid medium 64 traveling through baffle gap 99 is less than 0.0015, in other embodiments less than 0.0009, and in other embodiments less than 0.0006 m/s.

Distillation/Purification

Reactor effluent 63 exiting reactor 51 includes the desired chlorinated propane product (e.g. 1,1,1,3-tetrachloropropane) together with unreacted reactants (e.g. carbon tetrachloride and ethylene), reaction byproducts, and catalyst and catalyst residues. Reactor effluent 63 may therefore be referred to as crude chlorinated hydrocarbon stream (e.g. 1,1,1,3-tetrachloropropane crude). This crude is then purified by employing one or more distillation techniques to obtain a purified chlorinated propane stream (e.g. purified 1,1,1,3-tetrachloropropane).

Figure 4:
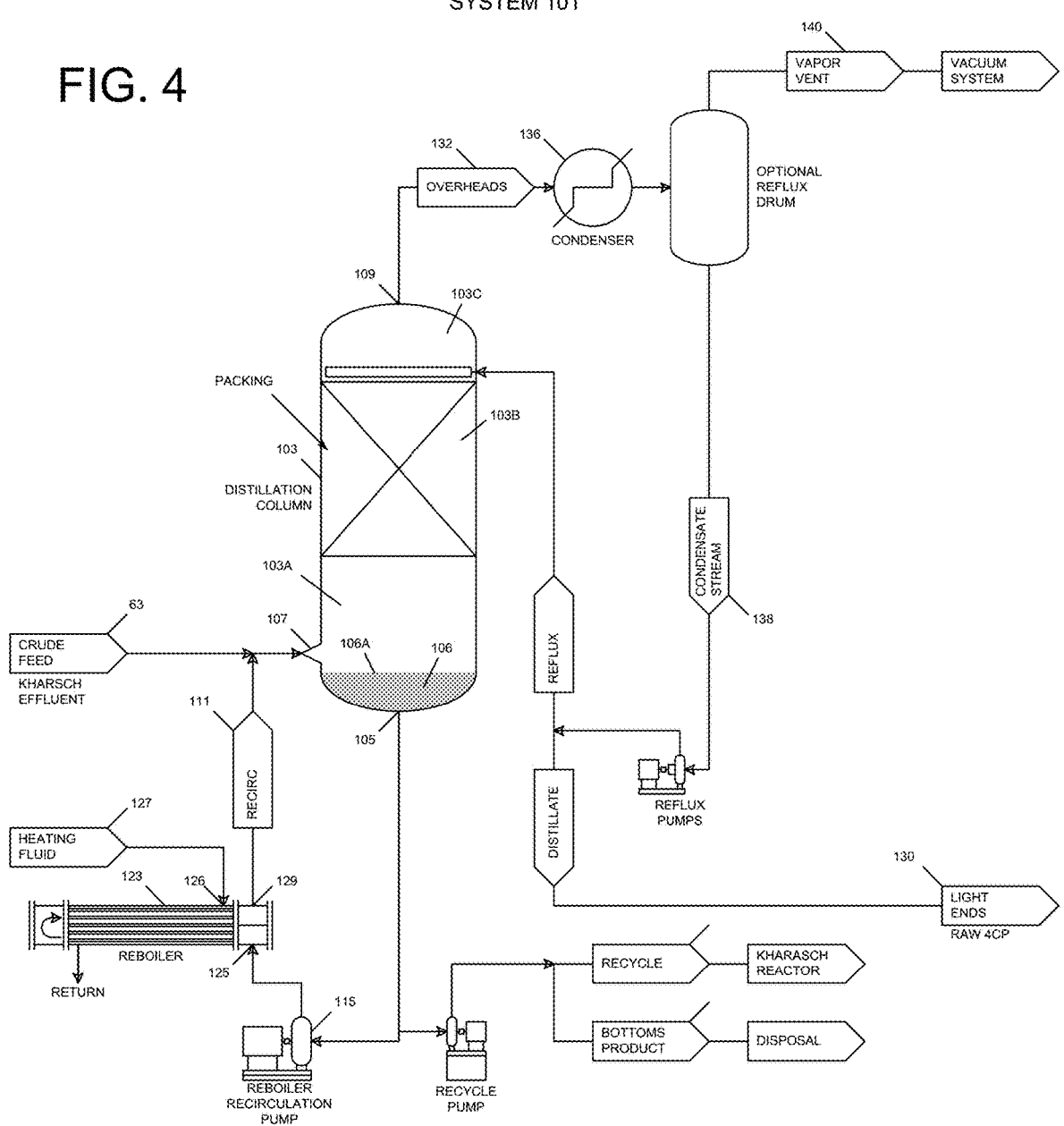
FIG. 4 is a schematic view of a system for purifying a crude stream of chlorinated propanes according to embodiments of the present invention.

The purification process of one or more embodiments can be described with reference to FIG. 4, which shows purification system 101 including distillation column 103 and reboiler 123. As generally known in the art, column 103 includes a bottom zone 103A, where column bottoms 106 in the form of liquid collect and form liquid level 106A, packing zone 103B, where packing materials and/or trays are located, and head space 103C through which vapor passes out of column 103.

In one or more embodiments, reboiler 123, which may also be referred to as a forced recirculation boiler 123, may include a single or multi-pass reboiler. In particular embodiments, as will be described herein below, a heating fluid or media travels shell side through reboiler 123. Practice of the present invention is not limited by the type of heating fluid employed and may include, for example, steam.

Distillation column 103 and reboiler 123 are in fluid communication via reboiler loop 111. Crude 63 enters column 103 at bottom 103A at or near liquid level 106A, where crude 63 becomes included in column bottoms 106 at the bottom of distillation column 103. Column bottoms 106 (which include the target chlorinated propanes) enter loop 111 from outlet 105. The velocity of column bottoms 106 flowing through loop 111 is regulated by, for example, pump 115. In one or more embodiments, the velocity of the column bottoms flowing through loop 111 is maintained at a rate sufficient to reduce tube wall temperatures within reboiler 123 and thereby inhibit reactions and/or the formation of deposits within reboiler 123. Column bottoms 106 enter reboiler 123 at inlet 125 and circulate tube side within reboiler 123. In one or more embodiments, the velocity of column bottoms 106 through reboiler 123 is at least 1, in other embodiments at least 3, and in other embodiments at least 5 m/s. In these or other embodiments, the velocity of column bottoms 106 through reboiler 123 is from about 1 to about 20, in other embodiments from about 2 to about 12, and in other embodiments from about 3 to about 9 m/s.

As suggested above, column bottoms 106 travel tube side through reboiler 123 where they are subjected to heat that is transferred from heating fluid steam 127 (e.g. steam) introduced through inlet 126 shell side of bottoms 106. In one or more embodiments, heat flux across the tubes within reboiler 123 is less than 44, in other embodiments less than 33, and in other embodiments less than 22 kW/m². In these or other embodiments, the heat flux across the tubes within reboiler 123 is from about 5 to about 44, in other embodiments from about 7 to about 33, and in other embodiments from about 10 to about 22 kW/m².

Column bottoms 106 exit reboiler at exit 129, as a heated liquid, and are injected into column 103 at inlet 107, which is positioned below packing zone 103B; in particular embodiments, column bottoms 106 enter at or near liquid level 106A. Column bottoms 106 leaving reboiler 123 through outlet 129 are heated to an extent that they will flash (i.e. boil) due to pressure differentials experienced upon entry into column 103. Also, as suggested by FIG. 4, reboiler 123 may be located at a lower elevation relative to the bottom of distillation column 103 to thereby provide sufficient hydrostatic pressure and thereby prevent premature boiling of the column bottoms within reboiler 123. Accordingly, the combination of fluid velocity, heat reflux within reboiler 123, and the pressure maintained within loop 111 serve to inhibit reactions and/or the formation of deposits onto the tube walls or within distillation column 103.

As the skilled person will appreciate, the desired chlorinated hydrocarbons will exit distillation column 103 as a vapor stream 132 through vapor outlet 109 of distillation column 103. Vapor stream 132 may then be routed through condenser 136, which causes the condensation of the desired chlorinated hydrocarbon 138 (e.g. 1,1,1,3-tetrachloropropane), which may also be referred to as condensate stream 138, while allowing lighter materials (as well as uncondensable materials) to exit as a light-end stream 140. A portion of condensate stream 138 may be routed back to column 103 via a distributor (not shown) and into head space 103C to reflux the packing. The remainder of condensate 138 is collected as the desired product. Depending on the desired level of purification, further distillation and purification of condensate stream 138 can be accomplished in downstream processing.

Various modifications and alterations that do not depart from the scope and spirit of this invention will become apparent to those skilled in the art. This invention is not to be duly limited to the illustrative embodiments set forth herein.

What is claimed is:

1. A process for producing chlorinated propanes, the process comprising:
    (i) reacting carbon tetrachloride with ethylene within a tank reactor that includes a liquid reaction mixture and a headspace above the reaction mixture wherein ethylene gas diffuses from the liquid reaction mixture into the headspace while agitating the reaction mixture, and
    (ii) transferring ethylene within the headspace back into the reaction mixture through a conduit within a mixing device that agitates the reaction mixture.

2. The process of claim 1, wherein the mixing device is an aspirating agitator.

3. The process of claim 1, wherein the mixing device is operating at a power to volume ratio of at least 10 kW/m².

4. A process for producing chlorinated propanes, the process comprising:
    (i) continuously agitating a mixture of an insoluble or partially soluble catalyst or catalyst precursor and carbon tetrachloride within a mix tank to thereby form a continuously agitated slurry,
    (ii) charging the continuously agitated slurry from the mix tank to a reactor,
    (iii) charging an olefin to the reactor,
    (iv) reacting the carbon tetrachloride with the olefin in the presence of the insoluble or partially soluble catalyst or catalyst precursor within a liquid reaction mixture within the reactor.

5. The process of claim 4, wherein said step of continuously agitating takes place within a continuously-stirred slurry tank.

6. The process of claim 4, wherein said step of continuously agitating is caused by continuously circulating the slurry through a slurry loop.

7. The process of claim 4, wherein the catalyst is iron powder.

8. The process of claim 4, wherein the olefin is ethylene.

9. The process of claim 6, wherein the slurry loop is maintained at a pressure in excess of the pressure within the reactor.

10. The process of claim 6, wherein the temperature of the slurry within the slurry loop is maintained at a temperature below the boiling point of carbon tetrachloride.

11. The process of claim 7, wherein the concentration of iron powder within the slurry is from about 0.02 to about 5.0 wt %.

12. A process for preparing chlorinated propanes, the process comprising:
(i) reacting carbon tetrachloride with an olefin in the presence of an insoluble or partially soluble catalyst or catalyst precursor within a liquid reaction mixture being continuously stirred within a tank reactor, and
(ii) removing the chlorinated propane product from the tank reactor from a still zone within the reactor, wherein the still zone is formed by a still-zone baffle.

13. The process of claim 12, wherein the still-zone baffle is defined by three internal walls and the wall of the reactor, which thereby provides the still zone, and wherein the still-zone baffle includes an opening proximate to the bottom of the reactor to thereby allow the reaction mixture to enter the still zone.

14. The process of claim 12, wherein the catalyst or catalyst precursor is iron powder.

15. The process of claim 12, wherein the velocity of the liquid reaction mixture traveling through the still zone is less than 0.0015 m/s.

16. The process of claim 12, wherein the liquid reaction mixture is removed from the reactor through a conically-shaped effluent nozzle.

17. A process for purifying a crude chlorinated propane product stream, the process comprising:
(i) providing a crude chlorinated propane product stream including iron and optionally iron compounds, and
(ii) heating the crude product stream within a reboiler operating at conditions that inhibit the reaction or formation of deposits within a distillation column and the reboiler, wherein the velocity of the crude product stream through the reboiler is from about 1 m/s to about 20 m/s, and wherein the reboiler includes tubes and the heat flux across the tubes is from about 5 $kW/m^2$ to about 44 $kW/m^2$, and
(iii) distilling the crude product stream with the distillation column.

18. The process of claim 17, wherein the reboiler is a forced circulation reboiler in fluid communication with a distillation column.

19. The process of claim 17, wherein the crude product stream travels through the tubes of the reboiler.

* * * * *